United States Patent [19]
Manser et al.

[11] Patent Number: 4,764,586
[45] Date of Patent: Aug. 16, 1988

[54] INTERNALLY-PLASTICIZED POLYETHERS FROM SUBSTITUTED OXETANES

[75] Inventors: Gerald E. Manser, Folsom, Calif.; Graham C. Shaw; Graham C. Shaw, III, both of Garland, Utah

[73] Assignee: Morton Thiokol, Inc., Chicago, Ill.

[21] Appl. No.: 925,659

[22] Filed: Oct. 29, 1986

[51] Int. Cl.⁴ .................. C08G 65/22; C06B 45/10
[52] U.S. Cl. ................... 528/362; 149/19.4; 149/19.6; 528/417
[58] Field of Search ............ 149/19.4, 19.6; 528/417, 362

[56] References Cited

U.S. PATENT DOCUMENTS

| | | | |
|---|---|---|---|
| 3,925,505 | 12/1925 | Sextro et al. | 525/472 |
| 4,234,364 | 11/1980 | Robinson | 149/19.4 |
| 4,393,199 | 7/1983 | Manser | 528/417 |
| 4,405,762 | 9/1983 | Earl et al. | 149/19.4 |
| 4,482,410 | 11/1984 | Stephens et al. | 149/19.4 |
| 4,482,411 | 11/1984 | Stephens et al. | 149/19.4 |
| 4,483,978 | 11/1984 | Manser | 528/408 |
| 4,707,540 | 11/1987 | Manser et al. | 528/362 |

FOREIGN PATENT DOCUMENTS

| | | | |
|---|---|---|---|
| 619416 | 5/1961 | Canada | 528/417 |
| 758450 | 10/1956 | United Kingdom | 528/417 |

OTHER PUBLICATIONS

Miyamura, *Chem. Abs.*, 90, Abs. #64498j (1979).

*Primary Examiner*—Edward A. Miller
*Attorney, Agent, or Firm*—Wayne E. Nacker; Gerald K. White

[57] ABSTRACT

Internally plasticized elastomeric binders for projectile propellants are cured polyethers containing THF, CYMMO plus BMEMO, BEEMO and/or OMMO mer units. The polyethers are fluid at room temperature and are miscible with nitrate ester plasticizers. Propellant binders prepared from these polyethers are curable, have low $T_g$'s, good mechanical properties, and $I_{sp}$'s comparable to PEG-based binders.

17 Claims, No Drawings

INTERNALLY-PLASTICIZED POLYETHERS FROM SUBSTITUTED OXETANES

The Government has rights in this invention pursuant to Contract No. F04611-82-C-0065 awarded by the U.S. Air Force.

The present invention is directed to novel polyethers, particularly for use in binder formulations for high-energy. nitrate ester-plasticized propellants.

BACKGROUND OF THE INVENTION

Solid propellants for rocket motors or the like include a high-energy fuel material, an oxidizer as required, and an elastomeric binder matrix in which the fuel material and oxidizer are dispersed and immobilized. Advantages of solid fuels in which an elastomeric binder material spatially immobilizes the fuel material and oxidizer are well known. The polymeric binder, however, represents a limitation in achieving maximum energy from a solid propellant in that the materials used in the binder burn with substantially lower energy than does the fuel material. It is desirable to minimize as much as possible the energy limitation that the binder material places on propellant formulations. Stated in an alternative manner, it is desirable that the binder burn along with the fuel material to release as much energy as possible. Achievement of binder energy value must be consistent with necessary characteristics of a binder, such as good elastomeric qualities and high mechanical strength parameters, particularly good stress and strain characteristics Nitrate ester plasticizers, such as nitroglycerine (NG), trimethylol ethane trinitrate (TMETN) and butanetriol trinitrate (BTTN) are generally included along with the polymeric binder. The nitrate ester plasticizers enhance the elastomeric properties of the binder and are in themselves high-energy materials which contribute to the energy of the binder system and the propellant as a whole.

In selecting a binder polymer, the energy that is released when it is burned is an important consideration. If a nitrate ester plasticizer is included in the propellant formulation, it is a further requirement that the binder polymer be compatible with the nitrate ester plasticizer; otherwise the plasticizer will weep, i.e., flow and settle out from the binder. Certain polymers which have sufficiently high energies and would otherwise be desirable elastomers for binders cannot be used in certain binder systems due to their incompatibility or immiscibility with nitrate ester plasticizers. Hydrocarbon elastomers, for example, are inherently relatively high in energy; but are immiscible with nitrate esters. A potential binder polymer is a polyether prepared from tetrahydrofuran (THF), having high load-bearing capability and low glass transition temperature ($T_g$); however, polymers prepared from THF polyethers are also immiscible with nitrate esters.

Propellant binders have been formed of polyethylene glycol (PEG) and polycaprolactone (PCP) and mixtures thereof. A PEG-based binder is more miscible with nitrate esters than is a THF-based binder, but insufficiently so for many propellant applications, and PEG-based binders are lower in energy than THF-based polymers. PCP-based binders have good miscibility with nitrate ester plasticizers, but PCP is substantially lower in energy than most other binder materials, tending to significantly reduce the energy value of the solid propellant as a whole.

In view of the above, there exists a need for new polymer-based elastomers having elastomeric and strength characteristics suitable for use as propellant binders, and which are inherently sufficiently high in energy and which are also miscible with nitrate esters.

U.S. Pat. No. 4,483,978 issued to G. E. Manser, the teachings of which are incorporated herein by reference, describes energetic copolymers and methods of making the same. The copolymers described in the '978 patent include copolymers of tetrahydrofurans and oxetanes having energetic pendent groups, such as azido, nitro and nitrato groups. The '978 patent teaches that the copolymers may be further copolymerized with a trifunctional substance to produce an elastomeric binder for a rocket propellant.

Copolymers, such as the THF/oxetane copolymers described in the '978 patent, are generally advantageous relative to homopolymers because the second mer unit, even in relatively small amounts, substantially reduces stereoregularity. Homopolymers having a high degree of stereoregularity exhibit substantial chain-folding, resulting in a compact structure which tends to be crystalline or highly viscous. Poly(THF) exhibits a high degree of crystalline structure. Poly(3-cyanomethyl-3-methyloxetane) is highly viscous, and thus, unsuitable for most propellant purposes.

Despite the general teaching in the '978 patent that THF/oxetane copolymers are generally useful in producing high-energy elastomeric binders for rocket propellants or the like, problems have been encountered in developing actual binder systems. Although there is ample description in the '978 patent of various copolymers formed from oxetane and tetrahydrofuran monomers, there is no example of a rocket propellant formulated with a binder that incorporates any such copolymer.

A problem which has been encountered when attempting to fabricate propellants from THF/oxetane copolymers is the tendency of the copolymers to have high viscosities. High-viscosity copolymers in an uncured propellant formulation with high-solids loading may be excessively viscous for processability. In preparing solid propellant formulations, relatively high levels of external plasticizers are used to decrease uncured formulation viscosity. Plasticizers which are energetic, such as nitrate ester plasticizers, are desirable in a propellant as they enhance the performance of the propellant. However, there is a limit to the amount of plasticizer which can be retained by any cured elastomer without the plasticizer migrating or "weeping" from the cured elastomer; hence, the problem of high polymer viscosity cannot necessarily be fully overcome through the use of external plasticizers.

The tendency to high viscosities of THF/oxetane polymers is attributable to a substantial degree of chain-packing. Chain-packing is the tendency for polymer molecules to closely associate with similar polymer molecules; this retards relative motion between the polymer molecules.

It would be desirable to provide THF/oxetane polymers having lower viscosities and further having other desirable characteristics which oxetane mer units may impart. For propellant formulations or the like, it is particularly desirable to have low-viscosity polymers which are miscible with relatively high proportions of nitrate ester plasticizers. It is further desirable that polymers for propellant formulations or the like have relatively high energies so as to contribute to the performance of the propellant.

SUMMARY OF THE INVENTION

In accordance with the present invention, polyethers are provided which are hydroxyl-terminated terpolymers (or higher number polymers) of tetrahydrofuran (THF) and two or more oxetanes. The heteropolymers are curable with isocyanates and cross-linking agents to form elastomers having good elastomeric and strength characteristics, and in particular, to form elastomers suitable as binders for solid propellants or the like. The THF mer units provide the heteropolymer with relatively high energy and good mechanical characteristics. A first oxetane mer unit is selected for having pendant groups which impart desirable characteristics to the heteropolymer, e.g., nitrate ester plasticizer-miscibility and relatively high energy for propellant formulation use. A second oxetane mer unit is selected having bulky pendant groups which space polymer molecules apart from each other and thereby "internally plasticize" the polymer. Oxetane mer units which serve as "internal plasticizers" have pendant groups having a total of between about 8 and about 14 carbon atoms.

In particular embodiments of the invention, terpolymers and higher number heteropolymers of THF, 3-cyanomethyl-3-methyloxetane (CYMMO) 3,3-bis[(2-methoxy-ethoxy)-methyl]oxetane (BMEMO), 3-octoxymethyl-3-methyloxetane (OMMO), and 3,3-bis[(2-ethoxy-ethoxy)-methyl]oxetane (BEEMO) are synthesized.

DETAILED DESCRIPTION OF CERTAIN PREFERRED EMBODIMENTS

The invention provides heteropolymers of THF and two or more oxetanes. The THF mer units provide good elastomeric and strength characteristics; one of the oxetane mer units imparts desired functional characteristics to the heteropolymer; and a second oxetane mer unit having bulky side chain groups internally plasticizes the heteropolymer. Internal plasticization reduces interaction or packing of polymer molecules, reducing viscosity of the heteropolymer. Preferred heteropolymers in accordance with the invention are liquid at room temperature and have relatively low processing temperature viscosities. Consequently, formulations containing internally plasticized heteropolymer, external plasticizer and high solids loading have sufficiently low viscosities for processability.

The heterpolymers are hydroxyl-terminated and are curable with isocyanates through chain extension and are cross-linkable to form elastomers. Oxetane mer units of heteropolymers used to form binders for propellants or the like preferably have pendant group which impart nitrate ester-miscibility to the heteropolymer and have relatively high energies so as to contribute to the performance of the propellant. The lubricity imparted to the uncured heteropolymer through internal plasticization is also imparted to the cured elastomer. Elastomers which are internally plasticized tend to have low glass transition temperatures ($T_g$'s) and enhanced elongation.

As discussed above, the mer units of the polyethers which are residues of THF contribute to the elastomeric and physical characteristics of the cured binder and also contribute significantly to the energy of the binder. A cured propellant binder should have a Young's modulus of at least about 400 psi.

Particular functional properties of heteropolymers in accordance with the invention are provided by a first oxetane mer unit having side chain or pendant groups that impart particular characteristics to the heteropolymers. Also, a mixture of oxetane mer units may be used providing a combination of functional groups which impart a variety of characteristic properties to the polymer. For use in forming propellants or other high-energy materials, it is often desirable that oxetane mer units have characteristic pendant groups which are relatively high in energy. Because elastomers used as propellant binders are often plasticized with nitrate ester plasticizers, which both plasticize and contribute significantly to the performance of the propellants, oxetane mer units may be selected having pendant groups which impart miscibility of the heteropolymer with nitrate ester plasticizers. Examples of pendant groups which impart high energy and miscibility with nitrate esters are nitro, nitrato, nitramino and cyano. The invention is exemplified herein primarily by heteropolymers in which the first oxetane mer unit is CYMMO which contains a cyano moiety in a pendant group.

There has been found to be a tendency with polyethers which are copolymers of THF and certain oxetanes for chain-packing to occur, in which case the polyether may be crystalline or have an undesirable high viscosity at processing temperatures; whereupon an uncured propellant formulation containing the polyether has an undesirably high viscosity for workability, e.g., mixing and casting. This chain-packing effect is found to occur most frequently when the oxetane mer units have short side chains or pendant groups, typical of many of the more polar oxetanes selected for the nitrate ester-miscibility of their pendant groups.

In accordance with the invention, THF-oxetane heteropolymers are internally plasticized by incorporation of the second oxetane mer unit having a bulky pendant group or groups. Mixtures of oxetane mer units having bulky pendant groups may also be used to impart internal plasticization. The bulky pendant groups prevent the polymer molecules from packing close to each other and thereby reduce the viscosity of the heteropolymer. In cured elastomers, the bulky pendant groups impart a self-lubricating property to the elastomer. The degree to which the bulky pendant groups internally plasticize a heteropolymer depends upon a number of factors, such as the sizes of the pendant groups and the three-dimensional configuration which the pendant groups assume. For purposes of the present invention, the pendant groups of each internally plasticizing oxetane mer unit contain a total of between about 8 and about 14 carbon atoms. A lesser number of carbon atoms generally allows polymer chains to pack too closely, although pendant groups of any size will serve some spacing function. The size of the pendant group or groups cannot be too large or the pendant groups will themselves exhibit chain-folding and chain-packing, negating the intended internally plasticizing effect.

The second oxetane mer units, of course, also impart functional characteristics to the heteropolymer. It is advantageous if the second oxetane mer unit contributes to the desired characteristic properties of the first oxetane mer unit; however, heteropolymers in accordance with the invention may be balanced with appropriate molar ratios of THF, a first oxetane mer unit imparting selected characteristics to the heteropolymer and a second oxetane mer unit providing adequate internal plasticization. The molar percentage of THF depends upon the mechanical requirements, and to a lesser extent upon the energetic requirements of the heteropolymer and may range from about 10 to about 85 molar percent of the heteropolymer, and preferably between about 45 and about 80 molar percent. The first oxetane mer unit (or mixture of mer units), selected for pendant group characteristics, is generally provided in greater molar proportion than the second oxetane mer unit (or mixture of oxetane mer units), selected for pendant group bulk, generally comprising between about 10 and about 80 molar percent of the heteropolymer and preferably between about 10 and about 50 molar percent. The second oxetane mer unit (or mixture of internally plasticizing mer units) generally comprises between about 5 and about 40 molar percent and preferably between about 5 and about 10 molar percent. Heteropolyethers, in accordance with the present invention, also contain the residue of the polymerization initiator.

The hydroxyl-terminated heteropolymers are curable in a conventional manner with isocyanates through chain-extension and by cross-linkage with appropriate cross-linking agents to form elastomers. Although the prepolymers and elastomers formed therefrom have a variety of uses, of particular interest is the use of heteropolymer-based elastomers as binders for propellants or the like. As binders, the elastomers spatially immobilize propellant components distributed therein. If the first oxetane mer unit is nitrate ester-miscible, elastomeric binders may contain substantial proportions of nitrate ester plasticizers. Cured elastomeric binders in accordance with the invention have energies comparable with polyethylene glycol and have good elastomeric and strength properties.

The oxetane monomers useful in formulating polyethers in accordance with the present invention have the general formula:

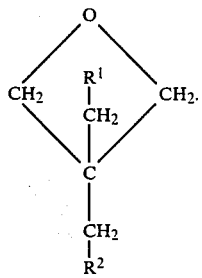

In the first oxetane used primarily to impart selected characteristics to the heteropolymer, $R^1$ or both $R^1$ and $R^2$ is or contains a functional group, including, but not limited to cyano, nitro, nitrato, nitramine, hydroxyl or azido. In the second oxetane used primarily for internal plasticization, $R^1$ and $R^2$ provide bulk, having between about 6 and about 12 carbon atoms (8–14 carbon atoms total, including the methylene groups bonded to the ring or backbone carbon). $R^1$ and $R^2$ may be a straight or branched, saturated or unsaturated hydrocarbon. $R^1$ and $R^2$ may also contain other groups, particularly including one or more ether linkages.

Numbering of the oxetane ring structure begins at the oxygen. When polymerized, the oxetanes provide mer units having the general formula:

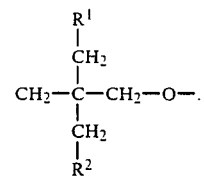

The invention is particularly exemplified herein by heteropolymers containing the following oxetanes: 3,3-Bis[(2-methoxy-ethoxy)-methyl]oxetane (BMEMO), wherein $R^1$ and $R^2$ are each) —$C_2H_4$—O—$CH_3$; 3-octoxymethyl-3-methyloxetane (OMMO), wherein $R^1$ is —H and R2 is —O—$C_8H_{17}$; 3,3-bis[(2-ethoxy-ethoxy)methyl]oxetane (BEEMO), wherein $R^1$ and $R^2$ are each 0—$C_2$ $H_4O$—$C_2H_5$; and 3-cyanomethyl-3-methyloxetane (CYMMO), wherein $R^1$ is —H and $R^2$ is —CN. CYMMO, having a pendant cyano group, contributes to nitrate ester-miscibility and is relatively high in energy; OMMO, BEEMO and BMEMO have pendant groups which internally plasticize the heteropolyethers.

Further examples of oxetanes useful for forming heteropolymers in accordance with the invention include but are not limited to:

| | |
|---|---|
| BEMO | 3,3-bis(ethoxymethyl)oxetane, |
| BCMO | 3,3-bis(chloromethyl)oxetane, |
| BMMO | 3,3-bis(methoxymethyl)oxetane, |
| BFMO | 3,3-bis(fluromethyl)oxetane, |
| HMMO | 3-hydroxymethyl-3-methyloxetane, |
| BAOMO | 3,3-bis(acetoxymethyl)oxetane, |
| BHMO | 3,3-bis(hydroxymethyl)oxetane, |
| OMMO | 3-octoxymethyl-3-methyloxetane, |
| CMMO | 3-chloromethyl-3-methyloxetane, |
| AMMO | 3-azidomethyl-3-methyloxetane, |
| BIMO | 3-3-bis(iodomethyl)oxetane, |
| IMMO | 3-iodomethyl-3-methyloxetane, |
| PMMO | 3-propynomethylmethyloxetane, |
| BNMO | 3,3-bis(nitratomethyl)oxetane, |
| NMMO | 3-nitratomethyl-3-methyloxetane, |
| BMNAMO | 3,3-bis(methylnitraminomethyl)oxetane, |
| MNAMMO | 3-methylnitraminomethyl-3-methyloxetane, and |
| BAMO | 3,3-bis(azidomethyl)oxetane. |

THF has the formula:

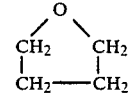

and forms mer units having the formula: —$CH_2$—$CH_2$—$CH_2$—$CH_2$—O—.

The THF mer units of the heteropolymer provide the cured elastomeric binder with desirable mechanical properties, particularly good stress and strain characteristics. Just as poly(THF) is incompatible with nitrate esters, THF mer units in the polyether do not contribute to miscibility with nitrate esters. Accordingly, if the heteropolymer must be miscible with nitrate esters, the relative amount of THF mer units incorporated in the heteropolymers to provide good mechanical characteristics and high energy is balanced against the requirement for nitrate ester-miscibility of the heteropolymers and the cured elastomers formed therefrom; which nitrate ester-miscibility is provided by oxetane mer units, particularly CYMMO mer units . Nitrate ester-miscibility and mechanical characteristics are also dependent upon the particular combination of oxetane monomers that are copolymerized with the THF, and the appropriate proportion THF mer units relative to oxetane mer units is therefore dependent upon the selection of oxetanes.

For forming propellants, it is necessary that the heteropolymer be sufficiently fluid at the mixing temperatures of the uncured propellant formulation to provide for workability of the uncured formulation, e.g., mixing, casting, etc. Uncured propellant formulations contain very high solids levels, e.g., between about 70 wt. percent and about 85%, and the viscosity of the high-solids formulation must be kept within workable limits. It is generally desired that an uncured propellant formulation have a Brookfield viscosity at the mixing temperature (typically in the range of 55° C.) of 50 kilopoise (KPS) or less, although it is possible to work propellant formulations of up to about 100 KPS without adding solvents, such as lacquers. The viscosity of an uncured propellant formulation depends upon the solids loading and the viscosity of the liquid components, including the polymer and plasticizer. As noted above, increasing the plasticizer-topolymer ratio in the uncured propellant formulation reduces the viscosity, but there is a limit to the amount of plasticizer which a cured elastomeric binder may stably retain. Accordingly, the polymer itself should have a sufficiently low viscosity. To this end, it is preferred that the polyether have a Brookfield viscosity at room temperature, e.g., 22° C., of about 7000 poise or less and preferably about 1000 poise or less. The viscosity of polyethers depends upon a number of factors. The chemical makeup of the mer units affects viscosity, but other factors, such as the three-dimensional configuration of the polymer and the physical interaction of the polymer molecules with each other may be more important. The fact that polymers in accordance with the present invention are heterogeneous with respect to mer unit content ensures stereoirregularity that inhibits chain-folding. The bulky pendant groups of the second oxetane mer unit inhibits chain-packing to reduce the viscosity of a heteropolymer formulated in accordance with the present invention.

Polymers must be curable, i.e., by reaction with isocyanates and cross-linking to form stable elastomers, and to this end, heteropolymers are produced having functionalities of at least about 2.0 and preferably at least about 2.3. Typically heteropolymers having functionalities of up to about 3.0 are produced, although heteropolymers having higher functionalities are considered to be within the scope of this invention. Polymer functionality is generally determined by the functionality of the initiator species.

For propellant formulations, it is typically desirable that the cured binder stably retain substantial amounts of nitrate ester plasticizer; typically a plasticizer-to-polymer ratio of at least about 2.0:1 is required and a ratio of at least about 2.5:1 preferred. By stably incorporated, it is meant that the plasticizer does not migrate significantly and does not weep from the binder. Nitrate ester-miscibility, where required, is provided primarily by the characteristic pendant group(s) of the first oxetane mer unit, although it may be desirable that the second, internally-plasticizing oxetane mer unit exhibit at least some miscibility with nitrate ester plasticizers.

Heteropolyethers of THF and two or more oxetanes, in accordance with the present invention, can be tailored to have specific physical properties by varying the relative molar ratios of the mer units. Of particular interest are low-temperature stress and strain parameters and also low $T_g$.

In accordance with a specific aspect of the present invention, polyethers are produced containing THF and CYMMO plus BMEMO, OMMO, BEEMO or mixtures of the internally-plasticizing oxetanes. Of these, OMMO is the most effective internal plasticizer, having a long, straight, hydrocarbon chain outward of the ether bond, the long hydrocarbon chain spacing polymer molecules apart. BMEMO and BEEMO each have two, but less bulky, pendant groups; mer units derived from these oxetanes are less effective internal plasticizers due to pendant group folding at the additional ether linkage. On the other hand, BMEMO and BEEMO are more hydrophilic than OMMO and thus more miscible with nitrate ester plasticizers. Heteropolymers, produced in accordance with the invention, utilize various molar ratios of THF and oxetanes to provide a balance of low-viscosity and nitrate ester-miscibility tailored to particular requirements.

A copolymer polyether prepared from equal molar amounts of THF and CYMMO is found to be miscible with nitrate esters, e.g., NG and TMETN, but the viscosity of the polymer and the resulting viscosity of the uncured propellant formulation are greater than is generally desired due to chain-packing, resulting in difficulty in processing and casting the uncured propellant formulation. Decreasing the molar ratio of CYMMO relative to THF in the polyether decreases the viscosity, but then the copolymer is less miscible with NG or TMETN. The invention addresses problems with this system by including the second oxetane mer unit, e.g., BMEMO, BEEMO, OMMO or mixtures thereof to provide internal plasticization and lower viscosity. In a THF/CYMMO/BMEMO polyether system, THF mer units are present at between about 45 and 85 molar percent and preferably between about 50 and about 70 molar percent; CYMMO mer units are present at between about 10 and about 50 molar percent and preferably at between about 30 and about 45 molar percent; and BMEMO, BEEMO and/or OMMO mer units are present at between about 5 and about 40 molar percent and preferably between about 5 and about 10 molar percent.

Cured binders formed from the heteropolymers of this invention are desirable in that they have glass transition temperatures ($T_g$'s) which are lower than PEG and PCP binders which typically have $T_g$'s in the −20° to −25° C. range. Binder material formed from poly(THF) also suffers from high $T_g$'s. It is considered an important advantage to have low $T_g$'s for propellant binders because many of such propellant systems, such as are used in missiles carried on the wings of airplanes, are subjected to much lower temperatures than the $T_g$'s of PEG and PCP. Any exposure of a cast propellant to a temperature below the $T_g$ of the binder may result in cracking of the cast propellant, exposing the projectile to potential malfunction, even if the projectile is subsequently warmed to above the $T_g$. Cured elastomeric binders incorporating polyethers prepared in accordance with the present invention have achieved $T_g$ values of −37° to −54° C. Internal plasticization contributes to low $T_g$'s.

Liquid heteropolymers in accordance with the present invention, are advantageous from a workability standpoint relative to PCP, PEG, and PCP/PEG mixtures, which are presently the polymers of choice in high-energy propellants containing nitrate ester plasticizers. PCP and PEG are waxy and solid at room temperature, and must be either solubilized in a solvent or heated to above their melting temperature in order to be used in workable, uncured propellant formulations. Liquid heteropolymers provide ease of processing in the uncured propellant formulations, eliminating the need to prepare and store lacquers which are commonly used to prepare solutions of solid polymers and nitrate esters.

Generally, heteropolymers are prepared, in accordance with the invention, by mixing THF and the oxetanes in desired molar ratios, and then adding an initiator or initiator mixture of appropriate functionality. Preferred chain initiators have a functionality in the range of about 3 or higher. A presently preferred trifunctional polymerization initiator for forming polyethers is a trimethylol propane-boron trifluoride-etherate complex.

Additional polymerization initiators which are complexes of organic preinitiator precursors and catalysts, such as those described in above-identified U.S. Pat. No. 4,483,978, may also be used. The polyethers may be formed from a solution of the oxetane monomers in THF without additional solvent. However, where excessive precipitation of polyether from THF proves to be limiting of polyether formation, polymerization may be performed in a suitable solvent, such as methylene chloride.

Chain elongation continues until substantial, e.g., greater than about 85%, exhaustion of the monomers. The length of the chains is largely dependent upon the molar equivalents of monomers (m) and the initiators (n), the average chain length being approximately m/n mer units long. Distribution of mer units throughout the polymer chains and polydispersity of the chains depends upon specific conditions of polymerization. Generally, polyethers in accordance with the invention have polydispersities of between about 1.5 and about 2.5.

Generally, for use in propellant binders, polyether chains are prepared having molecular weights (weight average) of between about 4000 and about 12,000 and molecular weights (number average) of between about 1500 and about 6000. The polyethers have equivalent weights (gram/equivalent) of between about 900 and about 2500.

The propellants are prepared using polyethers according to the present invention by conventional manner. Polyethers; nitrate ester plasticizers; fuel material, such as aluminum; and oxidizers, such as cyclotetramethylene tetranitramine (HMX), cyclotrimethylene trinitramine (RDX) or ammonium perchlorate (AP), are mixed together in appropriate proportions, and then a curative agent, in particular, a polyfunctional isocyanate, is added to cure the binder of the propellant formulation.

The isocyanate is generally added at between about 2 and about 10 weight percent relative to the heteropolyether and preferably between about 4 and about 6 weight percent relative to the heteropolyether in the propellant mix; however, this may vary depending upon the functionality and molecular weight of the isocyanate. It is preferred to use isocyanates for curing purposes having functionality in the range of about 3 to promote chain cross-linking in addition to chain elongation. The isocyanate may be used as a curative in conjunction with other cross-linking agents, such as trimethylolethane and trimethylolpropane. Curing is generally effected in the presence of a cure catalyst, dibutyl tin dilaurate being a preferred cure catalyst when using heteropolyethers in accordance with the present invention.

Propellants having binder systems produced in accordance with the present invention have specific impulses ($I_{sp}$'s) substantially above propellant systems having PCP binders, e.g., at least 0.5 sec. higher, and approaching propellant systems having PEG binders. The $I_{sp}$'s of the propellants are as high or higher than PEG/PCP binder systems commonly used in presently produced propellants.

Solid propellants prepared in accordance with the invention contain upwards between about 70% to about 85% solids, including fuel material and oxidizers. The binder, including cured elastomeric binder plus nitrate ester plasticizers, comprises between about 15 and about 30 weight percent of the propellant.

The $T_g$'s of the propellants are substantially determined by the $T_g$'s of the binder, and in accordance with the present invention are about 37° C. or below.

The invention will now be described in greater detail by way of specific examples.

EXAMPLE 1

3,3-Bis(methoxyethoxymethyl)oxetane (BMEMO)

To a 5 liter, three-neck flask, fitted with a reflux condenser, a stirrer, and a thermometer, were added 1824 g (24 mole) of 2-methoxyethanol followed by 139 g (6 mole) of sodium metal. The flask temperature was then raised to mild reflux and thus maintained until all the sodium had dissolved. At this time, 465 g (3 mole) of 3,3-bis(chloromethyl)oxetane was added and heating maintained for a further 24 hr. The mixture was then cooled to room temperature and the precipitated sodium chloride removed by filtration. The filtrate was dissolved in an excess of water, extracted with four portions of 500 ml methylene chloride, and then the combined organic layers were dried over magnesium sulfate. The solvent was then removed by evaporation and the required monomer isolated by fractional distillation, the fraction boiling at 85° C. and 0.1-mm pressure being collected. Redistillation from calcium hydride yielded 487 g of polymerizable grade monomer.

Elemental analysis calculated C, 56.4; H, 9.4, found C, 56.1; H, 9.8.

NMR(CDCL$_3$): w 3.36(s,CH$_3$); 3.57(d,OCH$_2$CH$_2$O) J=3; 3.69(s,CH$_2$O); 4.45(s,CH$_2$OCH$_2$).

EXAMPLE 2

3-Octoxymethyl-3-methyloxetane (OMMO)

Into a 5 liter, three-neck flask, fitted with a stirrer, reflux condenser, and nitrogen inlet tube, were placed 245 g (2.4 mole) of 3-hydroxymethyl-3-methyloxetane and 3000 ml of p-dioxane. To this solution 47 g (2 mole) of solid sodium metal was added, and the pot temperature was raised to reflux. Heat was maintained until all of the sodium had dissolved. 400 g (2 mole) of 1-bromooctane was added, and the reflux was resumed for 3 days. The mixture was cooled to room temperature, and the solid sodium bromide was filtered off using celite. The solvent was removed by evaporation and the product was distilled at 80° C. and 0.3-mm pressure. Redistillation from calcium hydride gave 231 g of polymerizable monomer, representing a 58 percent yield.

Element analysis calculated: C, 72.8; H, 12.2, found: C, 72.2; H, 12.6.

NMR(CDCL$_3$) o 0.86(t,CH$_3$); 1.03(m,(CH$_2$)$_6$; ring CH$_3$); 3.45(s,t(CH$_2$OCH$_2$)); 4,31, 4.49(ABq CH$_2$OCH$_2$) J=6.

EXAMPLE 3

3,3-Bis(ethoxymethyl)oxetane (BEEMO)

In a 12 liter, five-neck flask, fitted with a stirrer, reflux condenser, and dry nitrogen inlet tube, 8000 ml of dry 2-ethoxy ethanol followed by 717.6 g (31.2 mole) of sodium metal were placed. The temperature was maintained at mild reflux by the use of a cold water bath until all of the sodium had dissolved. To the reaction mixture was then added 1200 g (7.7 mole) of 3,3-bis (chloromethyl)oxetane, and the resultant mixture heated to mild reflux for 24 hr. After cooling to room temperature, the reaction products were quenched in 5000 ml of distilled water and then extracted with four portions of 500 ml of methylene chloride. The combined extracts were then dried over magnesium sulfate and the solvent removed by evaporation. Pure monomer was obtained by distillation. 1107 g of polymerizable grade monomer were obtained by redistillation from calcium hydride, representing a 63% yield.

EXAMPLE 4

3-Cyanomethyl-3-methyloxetane (CYMMO)

In a three-necked, 2-liter flask equipped with a mechanical stirrer, reflux condenser, and drying tube were combined 3-chloromethyl-3-methyloxetane (261 g, 2.2 M), sodium cyanide (160 g, 3.25 M), and 1.1 liter ethanol. The stirred mixture was refluxed for 60 hr. The reaction was cooled and filtered, and the filter cake was washed with a minimum amount of diethyl ether. The combined organic fractions were reduced in vacuum and the remainder was distilled to give 180 g (74%) of CYAMMO as a clear liquid, bp 74°-76° C./5 Torr. Elemental Analysis: Theory - C 64.86%, H 8.11%, N 12.61%; Found - C 64.88%, H 8.30%, N 12.6%.

EXAMPLE 5

Solution Polymerization 100 g of calcium hydride-dried methylene chloride is charged into a flame-dried, 500 ml resin flask which is maintained under a nitrogen atmosphere. To this flask is then added the calculated amount of freshly distilled 1,4-butanediol (BDO) followed by the calculated amount of borontrifluoride-etherate (1:2 mole ratio). This solution is allowed to react for 1 hr at room temperature. The reactor is then cooled to −10° C., and after 30 min a solution of the monomer(s) is added dropwise in methylene chloride (25 percent w/w concentration). The rate of addition usually ranges from 20 min. to 2 hr. If the rate of polymerization is unknown, the reaction is followed by gas chromatography (GC), until a conversion of greater than 90 percent is measured. At this time the contents of the flask are quenched with 50 ml of saturated brine solution. The organic phase is separated off, washed with 10-percent sodium bicarbonate solution, dried over magnesium sulfate, and evaporated to dryness at room temperature. The nature of the polymer dictates the method of purification. In most cases, a single precipitation from cold methanol yields an acceptable polymer.

EXAMPLE 6

Bulk (neet) Polymerization

Into a 500 ml, flame-dried resin flask, which is maintained under a nitrogen atmosphere, is charged a calculated amount of freshly distilled tetrahydrofuran (THF). While maintaining the flask at room temperature, a calculated amount of freshly distilled 1,4-butanediol is added followed by a calculated amount of borontrifluoride-etherate (the amount of BDO controls the final molecular weight). The flask is then cooled to 0° C., and after 60 min., the calculated amount of the second monomer is added in bulk. The rate of addition is governed by the reactivity ratio of the monomer pair, i.e., if the reactivity ratio of the second monomer is significantly different (higher) than that of THF, then the rate of addition is slower. The mole fraction of monomer 2 is maintained in the polymerization at a level which will give an apparently idealized copolymerization at the desired monomers-in-polymer composition. If the rate of polymerization is unknown, the polymerization is followed by GC, until a conversion of greater than 90 percent is measured. At this time, the polymerization is quenched, first by the addition of 100 ml of methylene chloride, followed by the addition of 50 ml of saturated brine solution. The organic layer is then separated, washed with a 100 ml sodium bicarbonate solution, dried over magnesium sulfate, and then evaporated to dryness. THF polymers are readily purified by precipitation from cold methanol.

EXAMPLE 7

CYMMO-BMEMO-THF Terpolymer (20/30/50)

All chemical reagents except the boron trifluoride etherate were dried; glassware was dried at 105° C. In a 500 ml reactor, was placed 36 gm (0.5 mol) THF and with stirring were added and dissolved 2206 ul (0.025 mol) BDO and 3.35 gm (0.025 mol) trimethylol propane. The solution was cooled to −15° C. and 15,381 ul (0.125 mol) boron trifluoride-etherate was added and stirred for 30 minutes.

22.2 gm (0.2 mol) CYMMO and 70.2 gm (0.3 mol) BMEMO were mixed, placed in a dropping funnel, and added dropwise to the reactor over four hours. The reaction was maintained at −15° C. for a further 18 hours.

The reaction was quenched by adding 200 ml methylene chloride followed by 50 mls saturated aqueous sodium chloride. The reactants were warmed to room temperature. The material was washed with two 100 ml portions of 10% sodium bicarbonate solution, dried over magnesium sulfate, filtered, and evaporated on a high vacuum line up to 80° C. overnight.

EXAMPLE 8

A series of monomer mixtures were prepared containing THF, CYMMO, BMEMO and OMMO in various molar ratios. The polyether formulations and properties of the polyethers and propellants formed therefrom are given in Table 1 below:

TABLE 1
POLYMER AND PROPELLANT PROPERTIES

| TYPE OF MER UNITS | MOLAR RATIO | POLYMER VISCOSITY POISE @ 22° CV | MOLECULAR Mn | WEIGHT Mn | EQUIVALENT WT (G/EQ) | FUNCTIONALITY | MISCIBLE IN NG & TMETN | PROPELLANT VISCOSITY KPS @ 55° C. |
|---|---|---|---|---|---|---|---|---|
| THF/CYMMO/BMEMO | 48/24/28 | 85 | 6560 | 2710 | 1570 | 1.7 | YES | 15 |
| THF/CYMMO/BMEMO | 50/35/15 | 608 | 8423 | 2360 | 1426 | 1.7 | YES | 21 |
| THF/CYMMO/BMEMO | 50/40/10 | 480 | 5250 | 2630 | 949 | 2.8 | YES | 20 |
| THF/CYMMO/BMEMO | 50/40/10 | 744 | 10670 | 4140 | 2288 | 1.8 | YES | 21 |
| THF/CYMMO/OMMO | 50/40/10 | 480 | 8890 | 3550 | 1267 | 2.8 | LIMITED | 28 |
| THF/CYMMO/OMMO | 50/40/5 | 5000 | 4489 | 1712 | 928 | 1.8 | LIMITED | 19 |
| THF/CYMMO/BMEMO | 40/45/5 | 6580 | 8591 | 2838 | 1557 | 1.8 | YES | 20 |
| THF/CYMMO/BMEMO/OMMO | 50/30/10/10 | 387 | 7285 | 2629 | 1203 | 2.2 | LIMITED | 17 |
| THF/CYMMO/BMEMO/OMMO | 50/40/5/5 | 1024 | 4420 | 1685 | 1065 | 1.6 | LIMITED | 19 |
| THF/CYMMO/BMEMO | 60/30/5 | 3140 | 8003 | 2936 | 1878 | 1.6 | YES | 18 |
| THF/CYMMO/BMEMO | 60/30/5 | 1488 | 7693 | 3787 | 1389 | 2.7 | YES | 20 |
| THF/CYMMO/BMEMO | 70/20/10 | 256 | 5800 | 3080 | 1340 | 2.3 | YES | 18 |
| THF/CYMMO | 80/20 | 2400 | 8300 | 5500 | 2500 | 2.2 | LIMITED | 24 |
| THF/CYMMO | 70/30 | 80000 | 9700 | 4800 | 2285 | 2.1 | LIMITED | 100 |

The molar ratios in Table 1 are the molar ratios of monomers which are mixed together prior to polyether formation. These ratios closely correspond to the final molar ratios of mer units in the polyethers. However, if BEEMO is used in place of BMEMO, the relative amount of THF incorporation to oxetane incorporation is substantially reduced, and additional THF must be added to the monomer mix in order to achieve a desired final ratio.

EXAMPLE 9

Propellant formulations were prepared using the THF/CYMMO 80/20 and THF/CYMMO/BMEMO 50/40/10 polyethers. For comparison, a conventional PCP-based propellant formulation was prepared from PCP-260, obtained from Union Carbide and Thanol, SF-6503, obtained from Texaco, which binder is a mixture of 60% Thanol/40% PCP by weight. In each case, the propellant formulation was 79% solids (Al (19%), HMX (10%), AP (50%)), 21% binder (polyether, NG, TMETN, and isocyanate curatives) with a plasticizer to polymer ratio of 2.5:1.

In the case of each of the polyether-based propellant system, the propellant mix was formulated and cured as follows: The polyether, NG and TMETN and aluminum were added into a mixing bowl. Mixing was for a 5 min. period, followed by scraping of the mix bowl, followed by a further 5 minute mix period. The AP is added in two portions with scrape-down between portions; total mix time is 20 min. The HMX is likewise added in two portions with scrape-down between portions; total mix time is 20 min. at 130° F. The mix is further mixed for 10 minutes under vacuum. The curative is then added, and mixing is continued for 1 hr. under vacuum at 130° F. Curing at 130° F. is effected over a 7 day period.

The Mechanical properties of the cured propellants are given in Table 2 below.

TABLE 2

| Polymer Type mer unit ratio | PROPELLANT MECHANICAL PROPERTIES THF/CYMMO 80/20 | | THF/CYMMO/BMEMO 50/40/10 | Thanol + PCP0260 | |
|---|---|---|---|---|---|
| Equivalent wt. (gm) | 2100 | 2500 | 1395 | 2117 + | 1490 |
| Polymer Functionality | 1.9 | 2.2 | 2.7 | 2.3 | 2.0 |
| Mechanical Properties: | | | | | |
| $E^{2.6}$ psi (77° F.) | 200 | 93 | 498 | 713 | |
| $\sigma_m$ psi (77° F.) | 34 | 23 | 51 | 80 | |
| $\sigma_m^c$ psi (77° F.) | 46 | 54 | 83 | 96 | |
| $\epsilon_m$ (%) (77° F.) | 30 | 110 | 63 | 34 | |
| $\epsilon_f$ (%) (77° F.) | 36 | 156 | 63 | 23 | |
| $\epsilon_m$ (%) −65° F. | 5 | 8 | 7 | 6 | |
| $\epsilon_f$ (%) −65° F. | 186 | 308 | 39 | 7 | |
| $\epsilon_m^c$ (%) −65° F. | 120 | 308 | — | 6 | |

EXAMPLE 10

Theoretical $I_{sp}$'s of propellants prepared in accordance with the present invention were calculated. In each case, the formulation assumed 79% solids (19% Al, 10% AP and 50% HMX), plasticizer (NG or TMETN or mixture thereof 14.6%) to polymer ratio of 2.3 to 1. Using the PCP formulation as a baseline, the net increase in $I_{sp}$ was determined, and the results are given in Table 3 below.

TABLE 3

Theoretical Performance Calculations
Tactical Formulation

| Polymer | Change In $I_{sp}$ |
|---|---|
| PCP (reference) | 0 |
| PEG | +0.9 |
| THF/CYMMO/BMEMO 50/45/5 or 50/40/10 | +0.7 |
| THF/CYMMO/BMEMO 65/35/5 | +0.8 |

From this table, it can be seen that the polyethers in accordance with the invention provide $I_{sp}$'s which are significantly elevated relative to PCP and approach the values obtained with PEG. Because many present day binder systems employ both PEG and PCP, compromising the energy value of PEG for the nitrate ester miscibility of PCP, the polyethers in accordance with the invention provide $I_{sp}$'s in line with currently used binder systems.

While the invention has been described in terms of certain preferred embodiments, modifications obvious to one with ordinary skill in the art may be made without departing from the scope of the present invention.

Various features of the invention are set forth in the following claims.

What is claimed:

1. A curable polyether comprising between about 10 and about 85 molar percent tetrahydrofuran mer units, between about 10 and about 80 molar percent of a first oxetane mer unit of mixture of oxetane mer units, and between about 5 and about 70 molar percent of a second oxetane mer unit or mixture of oxetane mer units, said first and second oxetane mer units in unpolymerized from each have the formula:

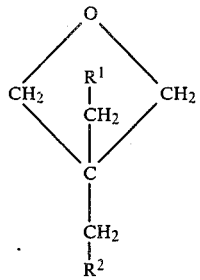

wherein in said first oxetane mer unit or mixture of mer units $R^1$ and/or $R^2$ is or contains moieties selected from the group consisting of cyano, azido, nitro, nitrato, nitramine and hydroxyl, and in said second oxetane mer unit or mixture of oxetane mer units $R^1$ plus $R^2$ contain between about 6 and about 12 carbon atoms.

2. A curable polyether in accordance with claim 1 wherein said first oxetane mer unit or mixture of oxetane mer units includes an energetic pendant group.

3. A curable polyether in accordance with claim 1 wherein said first oxetane mer unit or mixture of oxetane mer units includes a pendant group which promotes miscibility of said polyether with nitrate ester plasticizers.

4. A curable polyether in accordance with claim 1 wherein said first oxetane mer unit or mixture of mer units comprises 3-cyanomethyl-3-methyloxetane.

5. A curable polyether in accordance with claim 1 wherein said second oxetane mer unit or mixture of mer units comprises a mer unit selected from the group consisting of 3,3-bis[(2-ethoxy-ethoxy)methyl]oxetane, 3,3-bis[(2-methoxy-ethoxy)methyl]oxetane and 3-octoxymethyl-3-methyloxetane.

6. A curable polyether according to claim 1 wherein having a number average molecular weight of between about 1500 and about 6000.

7. A curable polyether in accordance with claim 5 wherein said first oxetane mer unit or mixture of oxetane mer units is selected from the group consisting of 3-cyanomethyl-3-methyl oxetane, 3-azidomethyl-3-methyloxethane, 3,3-bis(nitratomethyl) oxetane, 3-nitratomethyl-3-methyloxetane, 3,3-bis(methylnitraminomethyl) oxetane, 3-methylnitraminomethyl-3-methyloxetane, and 3,3-bis(azidomethyl) oxetane and mixtures thereof.

8. A curable polyether according to claim 1 having a weight average molecular weight of between about 4000 and about 12000.

9. A curable polyether according to claim 1 have a functionality of at least about 2.0.

10. A curable polyether according to claim 1 having a Brookfield viscosity at 22° C. of about 7000 poise or below.

11. A curable polyether comprising between about 45 and about 85 molar percent tetrahydrofuran mer units and between about 15 and about 55 molar percent of a mixture of two or more oxetane mer units, said oxetane mer units in unpolymerized form having the formula:

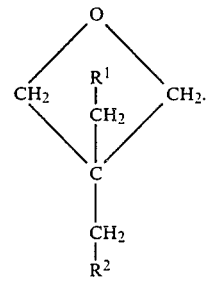

wherein $R^1$ and $R^2$ are selected from the group consisting of: —H; —O—$C_2H_4$—O—$C_2H_5$; —O—$C_2H_4$—O —$C_2H_4$—O —$CH_3$; —CN and —O —$(CH_2)$ n—$CH_3$, wherein n is 2–10, between about 10 and about 50 molar percent of said oxetane mer units being residues of 3-cyanomethyl-3-methyl-oxetane and between about 5 and about 50 percent of said oxetane mer units having $R^1$ plus $R^2$ containing between 6 and 12 carbon atoms.

12. A curable polyether according to claim 11 wherein having a number average molecular weight of between about 1500 and about 6000.

13. A curable polyether according to claim 11 having a weight average molecular weight of between about 4000 and about 12000.

14. A curable polyether according to claim 11 have a functionality of at least about 2.0.

15. A curable polyether according to claim 11 having a Brookfield viscosity at 22° C. of about 7000 poise or below.

16. A curable polyether comprising tetrahydrofuran mers at between about 45 and about 80 molar percent, 3-cyanomethyl-3-methyloxetane mers at between about 10 and about 50 molar percent and mers selected from the group consisting of 3-octoxymethyl-3-methyloxetane, 3,3-bis[(2-methoxy-ethoxy-methyl]oxetane, 3,3-bis[(2-ethoxy-ethoxy)methyl]oxetane and mixtures thereof at between about 5 and about 20 molar percent.

17. A curable polyether according to claim 16 comprising tetrahydrofuran mers at between about 50 and about 70 molar percent, 3-cyanomethyl-3-methyloxetane, mers at between about 30 and about 45 molar percent and mers selected from the group consisting of 3-octoxymethyl-3-methyloxetane, 3,3-bis[(2-methoxy-ethoxy)methyl]oxetane, 3,3-bis[(2-ethoxy-ethoxy)methyl]oxetane and mixtures thereof at between about 5 and about 10 molar percent.

* * * * *

UNITED STATES PATENT AND TRADEMARK OFFICE
CERTIFICATE OF CORRECTION

PATENT NO. : 4,764,586

DATED : August 16, 1988

INVENTOR(S) : Gerald E. Manser and Graham C. Shaw, III

It is certified that error appears in the above-identified patent and that said Letters Patent is hereby corrected as shown below:

<u>INVENTORS</u>: The inventors are only two as shown above. Please delete "Graham C. Shaw".

IN THE SPECIFICATION:

Column 1, line 10, after "ergy" change "." to --,--.
Line 33, after "tics" add --.--.

Column 6, line 15, change "R2" to --$R^2$--.

line 17, delete the space after "O—$C_2$" so that the formula will read --O—$C_2H_4$O—$C_2H_5$--.

Column 7, line 23, change "plasticizer-topolymer" to read --plasticizer-to-polymer--.

IN THE CLAIMS:

Column 15, line 20, after the word <u>unit</u> change "of" to --or--.
line 21, change "70" to --40--.
line 24, change "from" to --form--.
Column 16, line 8, change "have" to --having--.
line 41, delete "wherein".
line 46, change "have" to --having--.

UNITED STATES PATENT AND TRADEMARK OFFICE
CERTIFICATE OF CORRECTION

PATENT NO. : 4,764,586

DATED : August 16, 1988

INVENTOR(S) : Gerald E. Manser and Graham C. Shaw, III

It is certified that error appears in the above-identified patent and that said Letters Patent is hereby corrected as shown below:

Column 15, line 61, delete "wherein".

Signed and Sealed this

Twenty-eighth Day of November 1989

Attest:

JEFFREY M. SAMUELS

*Attesting Officer*  *Acting Commissioner of Patents and Trademarks*